(12) United States Patent
Wells

(10) Patent No.: US 6,455,734 B1
(45) Date of Patent: Sep. 24, 2002

(54) ANTAGONISTS OF THE MAGNESIUM BINDING DEFECT AS THERAPEUTIC AGENTS AND METHODS FOR TREATMENT OF ABNORMAL PHYSIOLOGICAL STATES

(75) Inventor: Ibert Clifton Wells, Omaha, NE (US)

(73) Assignee: Magnesium Diagnostics, Inc., Omaha, NE (US)

( * ) Notice: Subject to any disclaimer, the term of this patent is extended or adjusted under 35 U.S.C. 154(b) by 0 days.

(21) Appl. No.: 09/635,266

(22) Filed: Aug. 9, 2000

(51) Int. Cl.$^7$ ........................ C07C 233/11; A61K 31/16
(52) U.S. Cl. ........................ 564/157; 564/159; 514/616; 514/866
(58) Field of Search ................................ 564/157, 159; 514/616, 866

(56) References Cited

U.S. PATENT DOCUMENTS

| | | |
|---|---|---|
| 3,894,995 A | 7/1975 | Reske et al. |
| 4,144,244 A | 3/1979 | Brace |
| 4,331,570 A | 5/1982 | Klemarczyk et al. |
| 4,622,339 A | 11/1986 | Lieb et al. |
| 4,705,897 A | 11/1987 | Alexander |
| 5,268,359 A | 12/1993 | Harmar et al. |
| 5,491,140 A | 2/1996 | Bruns et al. |
| 5,492,927 A | 2/1996 | Gitter et al. |
| 5,525,624 A | 6/1996 | Gitter et al. |
| 5,563,133 A | 10/1996 | Hipskind |
| 5,565,568 A | 10/1996 | Cho et al. |
| 5,594,022 A | 1/1997 | Horwell et al. |
| 5,607,947 A | 3/1997 | Hipskind |
| 5,610,176 A | 3/1997 | Horwell et al. |
| 5,616,562 A | 4/1997 | Murphy et al. |
| 5,670,499 A | 9/1997 | Cho et al. |
| 5,684,033 A | 11/1997 | Cho et al. |
| 5,698,710 A | 12/1997 | Sisto et al. |

FOREIGN PATENT DOCUMENTS

| | | | |
|---|---|---|---|
| DE | 2065879 | * | 8/1976 |
| FR | 2166316 | * | 8/1973 |

OTHER PUBLICATIONS

Frickey, P.H., et al., "Preparation and Characterization of Monoclonal Antibodies to Substance P," *Hybridoma*, Nov. 6, 1991, 10:685–694.

Horwell, D.C., "Use of the Chemical Structure of Peptides as the Starting Point to Design Nonpeptide Agonists and Antagonists at Peptide Receptors: Examples with Cholecystokinin and Tachykinins," *Bioorganic & Medicinal Chemistry*, 1996, 4(10):1573–1576.

Mattingly, M.T., et al. "Decreased Cell Membrane Magnesium in Some Essential Hypertension Patients," *Clin. and Exper. Hyper.–Theory and Practice*, 1991, 13(1):65–82 (author's reprint enclosed–total of 20 pages).

Theodorsson–Norheim, E., et al., "Neuropeptide K: A Major Tachykinin in Plasma and Tumor Tissues from Carcinoid Patients," *Biochemical and Biophysical Research Communications*, 1985, 131(1)77–83.

Wells, I.C., et al., "Abnormal magnesium metabolism in two rat models of genetic hypertension," *Can. J. Physiol. Pharmacol.*, 1992, 70:1225–1229.

Edvinsson, L., et al., "Reduced levels of calcitonin gene–related peptide(CGRP) but not substance P during and after treatment of severe hypertension in man," *J. Human Hypertension*, 1989, 3:267–270.

Faulhaber, H.D., et al., "Substance P in Human Essential Hypertension," *J. Cardiovasc. Pharmacol.*, 1987, 10(Suppl. 12):S172–S176.

Meyer, P., and Marche, P., "Cell Membrane in Hypertension," *The American Journal of Medicinal Sciences*, Apr., 1988, 295(4):396–399.

Mori, K., et al., "Decreases in Substance P and Vasoactive Intestinal Peptide Concentrations in Plasma of Stroke–Prone Spontaneously Hypertensive Rats," *Jpn. Heart J.*, Nov., 1993, 34(6):785–794.

Resnick, L.M., et al., "Intracellular free magnesium in erythrocytes of essential hypertension: Relation to blood pressure and serum divalent cations," *Proc. Natl. Acad. Sci. USA*, Oct., 1984, 81:6511–6515.

Sanfilippo, J.S., et al., "Amniotic Fluid Levels of Substance P," *The Journal of Reproductive Medicine*, Aug, 1992, 37(8):733–736.

Takano, Y., et al., "Substance P immunoreactivity released from rat spinal cord after kainic acid excitation of the ventral medulla oblongata: a correlation with increases in blood pressure," *Brain Research*, 1984, 291:168–172.

* cited by examiner

*Primary Examiner*—Shailendra Kumar
(74) *Attorney, Agent, or Firm*—Rothwell, Figg, Ernst & Manbeck, p.c.

(57) ABSTRACT

This invention provides a class of therapeutic compounds and methods for the treatment of mammals of physiological disorders, for example a frequently occurring type of essential hypertension, which are associated with the decreased binding of magnesium to the plasma membranes of their cells. These methods consist of administering to a mammal in need of such treatment a compound selected from a series of disubstituted trans,trans-1,3-butadienes, 1,3-perhydrobutadienes, 1,2-disubstituted trans ethylenes, and 1,2-disubstituted ethanes and disubstituted propanes, each of which embodies, in common, the unique structural feature essential for the biological activity of these compounds. This invention also provides for pharmaceutical formulations that employ these novel compounds.

71 Claims, No Drawings

SEQUENCE LISTING

<160> NUMBER OF SEQ ID NOS: 4

<210> SEQ ID NO 1
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 1

Arg Pro Lys Pro Gln Gln Phe Phe Gly Leu Met
1               5                   10

```
<210> SEQ ID NO 2
<211> LENGTH: 3
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: AMIDATION

<400> SEQUENCE: 2

Gly Leu Met
1

<210> SEQ ID NO 3
<211> LENGTH: 4
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: AMIDATION

<400> SEQUENCE: 3

Phe Gly Leu Met
1

<210> SEQ ID NO 4
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: AMIDATION
<220> FEATURE:
<221> NAME/KEY: VARIANT
<222> LOCATION: (2)..(2)
<223> OTHER INFORMATION: "X" may be either F or V.

<400> SEQUENCE: 4

Phe Xaa Gly Leu Met
1               5
```

ANTAGONISTS OF THE MAGNESIUM BINDING DEFECT AS THERAPEUTIC AGENTS AND METHODS FOR TREATMENT OF ABNORMAL PHYSIOLOGICAL STATES

BACKGROUND OF THE INVENTION

This invention relates to therapeutic methods and compositions for the treatment of the cellular membrane magnesium binding defect, a defect associated with certain abnormal physiological states, e.g., sodium-sensitive essential hypertension and Type 2 insulin-resistant diabetes mellitus.

The applicant discovered, by studying essential, or primary, hypertension in humans and in two strains of rats with genetic hypertension, that a specific metabolic defect is critically involved with the occurrence of so-called "salt-sensitive", i.e. sodium ion sensitive, hypertension. This defect is the decreased binding of the magnesium ion (i.e., $Mg^{2+}$) within the plasma membranes of somatic cells, in particular smooth muscle cells.

As a direct consequence of this defect, intracellular concentrations of the magnesium ion, decrease while those of the sodium ion (i.e., $Na^+$) tend to increase due ostensibly to the increased passive permeability of the cell membranes for the latter ion. If the mammal's ability to remove the excess $Na^+$ from the intracellular compartment is also compromised, then, as a consequence, the intracellular concentration of calcium ion (i.e. $Ca^{2+}$) also increases and causes, in particular, the heightened contractility of the smooth muscle cells lining the peripheral blood vessels.

The contraction of these cells causes the lumens of these vessels to decrease and consequently the resistance to blood flow increases. To overcome this increased resistance, and thereby to maintain the requisite blood flow, the heart contracts more strongly, causing the pressure in the arteries to increase. This abnormal, increased blood pressure is recognized clinically as hypertension. Since this result stems directly from the seemingly increased passive permeability of the cell membrane to sodium ion, the hypertension is classified as being "sodium sensitive" and occurs in approximately 50 per cent of the essential hypertensive population which comprises about 25 percent of the population of the United States.

One general treatment proposed for the control of the blood pressure in essential hypertensive patients is the restriction of their dietary intake of salt (i.e., NaCl), the major source of sodium ion for the body. This measure is somewhat beneficial if the hypertension is salt-sensitive. However, if the hypertension is "salt-insensitive", the restriction of the salt content of the diet has no therapeutic value aside from the frequently observed, concomitant reduction of food intake, and may actually worsen the hypertension.

The applicant also demonstrated that the magnesium binding defect is caused by the lack, or at least the decreased concentration, of a component of normal blood plasma. When erythrocytes from either salt-sensitive, essential hypertensive humans or rats are incubated with blood plasma from analogous normotensive subjects, the magnesium binding defect in the plasma membranes of these cells is corrected and the abnormal concentrations of intracellular ions are normalized. The effective components of normal blood plasma are identified as the pentapeptide and its contained tetrapeptide which comprise the C-terminal region of the tachykinin known as "Substance P", the first mammalian produced tachykinin to be isolated and identified. It is composed of eleven amino acids joined by peptide linkages in the following sequence. Sequence No. 1: Arg-Pro-Lys-Pro-Gln-Gln-Phe-Phe-Gly-Leu-Met-$NH_2$. The derived pentapeptide and its contained tetrapeptide which correct the magnesium-binding defect have the following amino acid sequences, respectively. Sequence No. 2: Phe-Phe-Gly-Leu-Met-$NH_2$; Sequence No. 3: Phe-Gly-Leu-Met-$NH_2$. The applicant obtained evidence to indicate that the "general amino acid sequence" at the C-terminal region of mammalian-produced tachykinins is: Sequence No. 4, Phe-X(Phe, Val)-Gly-Leu-Met-$NH_2$, which comprises those pentapeptides and tetrapeptides occurring in mammalian blood plasmas that are derived from the tackykinins. The applicant has observed that they prevent the occurrence of the magnesium-binding defect in plasma membranes of somatic cells and also has demonstrated their in vivo effectiveness in correcting this defect in rats and the associated, salt-sensitive, essential hypertension.

The occurrence of the magnesium-binding defect in erythrocyte membranes also antagonizes, or "resists", the effect of insulin to promote the uptake of magnesium by these cells. The applicant has examined the erythrocytes from a number of patients with "adult onset" or Type 2 diabetes mellitus and has found the magnesium-binding defect to occur with a frequency greater than 90%. Thus, the magnesium-binding defect is a significant contributor to the causation of "insulin resistance", which in patients with Type 2 diabetes mellitus is, in most cases, considered to be the initiating cause of their diabetes.

The combination of the relationships of the magnesium-binding defect to salt-sensitive, essential hypertension, and to the characteristic insulin resistance of Type 2 diabetes mellitus, suggests a possible critical relationship of this defect with the occurrence of pre-eclampsia and eclampsia since salt-sensitive hypertension, insulin resistance, and overt diabetes mellius are among the prominent clinical features of these two life-threatening, physiological abnormalities of human pregnancy.

The pentapeptides and tetrapeptides discussed above occur in normal blood plasma and are believed to be derived in vivo by enzymatic degradation of the tachykinins produced by nerve tissue, as well as by other tissues. Their quantitation in blood plasma could provide useful information for the diagnosis of those pathological states with which the magnesium-binding defect is critically associated.

Ostensibily, these substances also are believed to be highly specific, naturally occuring therapeutic agents in contrast to the relatively non-specific therapeutic substances presently available for the treatment of abnormal physiological states such as salt-sensitive, essential hypertension. However, they are peptides and, as such, are generally observed to be metabolically unstable, and therefore are subject to the restricted routes of administration necessary for this class of substances. Consequently, this invention concerns the compositions and pharmacological applications of a new class of biologically stable, monopeptide compounds which are derived from butadienes, ethylenes, and propanes, which can be utilized to treat and/or to prevent those abnormal physiological states with which the magnesium-binding defect is critically associated.

SUMMARY OF THE INVENTION

This invention is a class of compounds represented by the Formula below (as well as their pharmaceutical acceptable salts) and therapeutic methods using such compounds for the treatment or prevention in mammals of physiological disorders which are associated with a deficiency of magnesium ion bound to the plasma membranes of their somatic cells.

DETAILED DESCRIPTION OF THE PREFERRED EMBODIMENTS

Compounds of this invention include those of the Formula $$\begin{array}{c} R_5 \\ \diagdown \\ R_6 \end{array} NCH_2 - \underset{R_3}{\overset{R_4}{X}} \underset{CON}{\overset{R_1}{\diagdown}} R_2$$

wherein:

$R_1$, $R_2$ and $R_5$ are independently selected from the group consisting of H and $C_1$–$C_2$ alkyl;

$R_3$ and $R_4$ are selected from $C_2$–$C_8$ alkyl;

$R_6$ is selected from H or the L-isomer (amino acid convention) of $R_7$—$(CH_2)_n$—$HC(NH_2)$—$CO$—;

wherein n is an integer from 0 to 3;

$R_7$ is selected from the group consisting of $C_3$–$C_6$ alkyl or aryl (unsubstituted or mono substituted with hydroxy, halo, amino, nitro, methyl or acetoxy), wherein said aryl is independently selected in each instance from the group consisting of phenyl, biphenyl, naphthyl, furanyl, pyrrolyl, thiophenyl, pyridinyl, indolyl, benzofuranyl, benzothiophenyl, quinolinyl, isoquinolinyl, imidazolyl, thiazolyl, pyrazinyl, primidinyl, purinyl, and pteridinyl; and X is independently selected from the group consisting of trans,trans >C=CH—HC=C<, trans >C=C<, and <C*H—(CH$_2$)$_m$—HC*< where C* is a chiral center and $R_3$ and $R_4$ are oriented L- and D-(amino acid convention) at these respective chiral centers, and where m=0, 1 or 2. This invention also includes pharmaceutically acceptable salts, solvates or prodrugs of compounds of the Formula above.

As used herein, the term "alkyl" refers to a straight or branched, monovalent, saturated aliphatic chain of carbon atoms, including normal, iso, neo or text. "Alkyl" includes but is not limited to, methyl, ethyl, propyl, isopropyl, butyl, isobutyl, sec butyl, tert butyl, amyl, isoamyl, neoamyl, hexyl, isohexyl, neohexyl, heptyl, isoheptyl, neoheptyl, octyl, isooctyl, neooctyl.

Although the free-base forms of the compounds of the above Formula may be used in the methods of the present invention, it is preferred to prepare and to use a pharmaceutically acceptable salt form. Thus, the compounds used in the methods of this invention form pharmaceutically acceptable acid addition salts with a wide variety of organic and inorganic acids, and include the physiologically acceptable salts which are often used in pharmaceutical chemistry. Such salts are also part of this invention.

The term "pharmaceutically acceptable salt" as used herein, refers to salts of compounds of the above formula which are substantially non-toxic to living organisms. Typical inorganic acids used to form such salts include hydrochloric, hydrobromic, hydroiodic, nitric, sulfuric, phosphoric, hypophosphoric and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, butyne-1,4-dioate, hexyne-1,4-dioate, caprate, caprylate, caproate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the chloride salt.

The pharmaceutically acceptable acid addition salts are typically formed by reacting a compound of the above Formula with an equimolar or an excess amount of acid. The reactants are generally combined in a mutual solvent such as diethyl ether or ethyl acetate. The salt normally precipitates out of solution within one hour to 10 days and can be isolated by filtration or the solvent can be stripped off by conventional means.

The pharmaceutically acceptable salts generally have enhanced solubility characteristics compared to the compound from which they are derived, and thus are often more amenable to formulations as liquids or emulsions.

It should be recognized that the particular counter-ion forming a part of any salt of this invention is usually not of a critical nature, so long as the salt as a whole is pharmaceutically acceptable and as long as the counter-ion does not contribute undesired qualities to the salt as a whole.

This invention further encompasses the pharmaceutically acceptable solvates of the compounds of the above Formula. Many of them can combine with solvents such as water, methanol, ethanol and acetonitrile to form pharmaceutically acceptable solvates such as the corresponding hydrate, methanolate, ethanolate and acetonitrilate.

Preferred compounds of this invention for use with the methods described herein are those of the above Formula wherein $R_1$, $R_2$ and $R_5$ are H;

$R_3$ and $R_4$ are independently selected from the group consisting of n-butyl, n-amyl and n-hexyl;

$R_6$ is selected from the group consisting of L-phenylglycine and L-valine.

X is selected from the group consisting of trans,trans >C=CH—HC=C<, trans >C=C<, >C*H—(CH$_2$)$_m$—C*H<, (wherein the "*" represents a chiral carbon, and m=0, 1 or 2); or a pharmaceutically acceptable salt or solvate thereof.

The present invention is also a method of treating a patient with a physiological disorder critically associated with the magnesium binding defect by administering to such a patient a pharmacologically effective amount of a composition that includes a compound of the above Formula.

It will be appreciated that certain compounds of the above Formula can possess an asymmetric carbon atom(s) and are thus capable of existing as enantiomers. Unless otherwise specified, this invention includes such enantiomers, including racemates. The separate enantiomers may be synthesized from chiral starting materials, or the racemates can be resolved by procedures that are well known in the art of chemistry such as chiral chromatography, fractional crystallization of diastereometric salts and the like.

Compounds of the above Formula can also exist as geometric isomers (Z or E), the Z isomer is preferred.

The oral forms of compositions containing compounds of the above Formula are most preferred although compounds of this invention may be formulated into pharmaceutical compositions, together with pharmaceutically acceptable carriers, in solid or liquid form, for rectal and topical, as well as for oral, administration.

The pharmaceutical compositions of this invention are preferably packaged in a container (e.g., a box or bottle, or both) with suitable printed material (e.g., a package insert) containing indications, directions for use, etc.

Compounds of this invention can be prepared by a variety of procedures well known to those of ordinary skill in the art.

The particular order of steps required to produce the compounds of the above Formula is dependent upon the particular compound being synthesized, the starting compound, and the relative lability of the intermediate moieties.

The compounds employed in this invention can be prepared by the following general schemes of reactions; the substituted trans, trans butadiene and trans ethylene structures are most preferred and, in general, are the precursors to the substituted perhydrobutadiene, perhydroethylene-based, and propane-based compounds which are also represented by the above Formula.

Reactions Sequence for the Synthesis of Trans, Trans-1,3-Butadiene Based Compounds of Formula

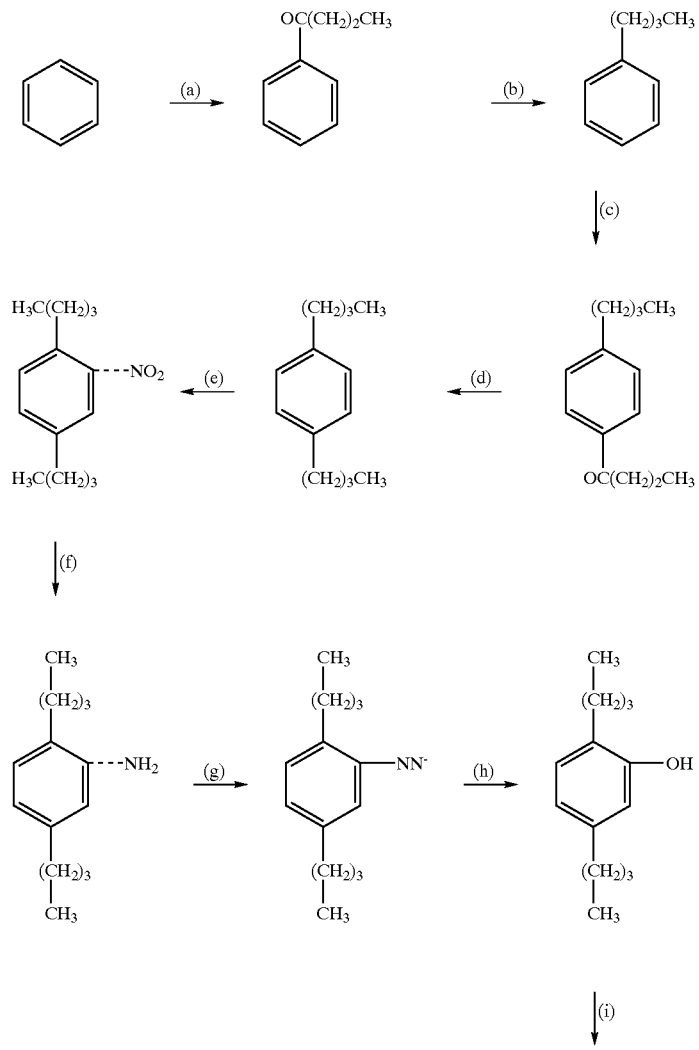

-continued

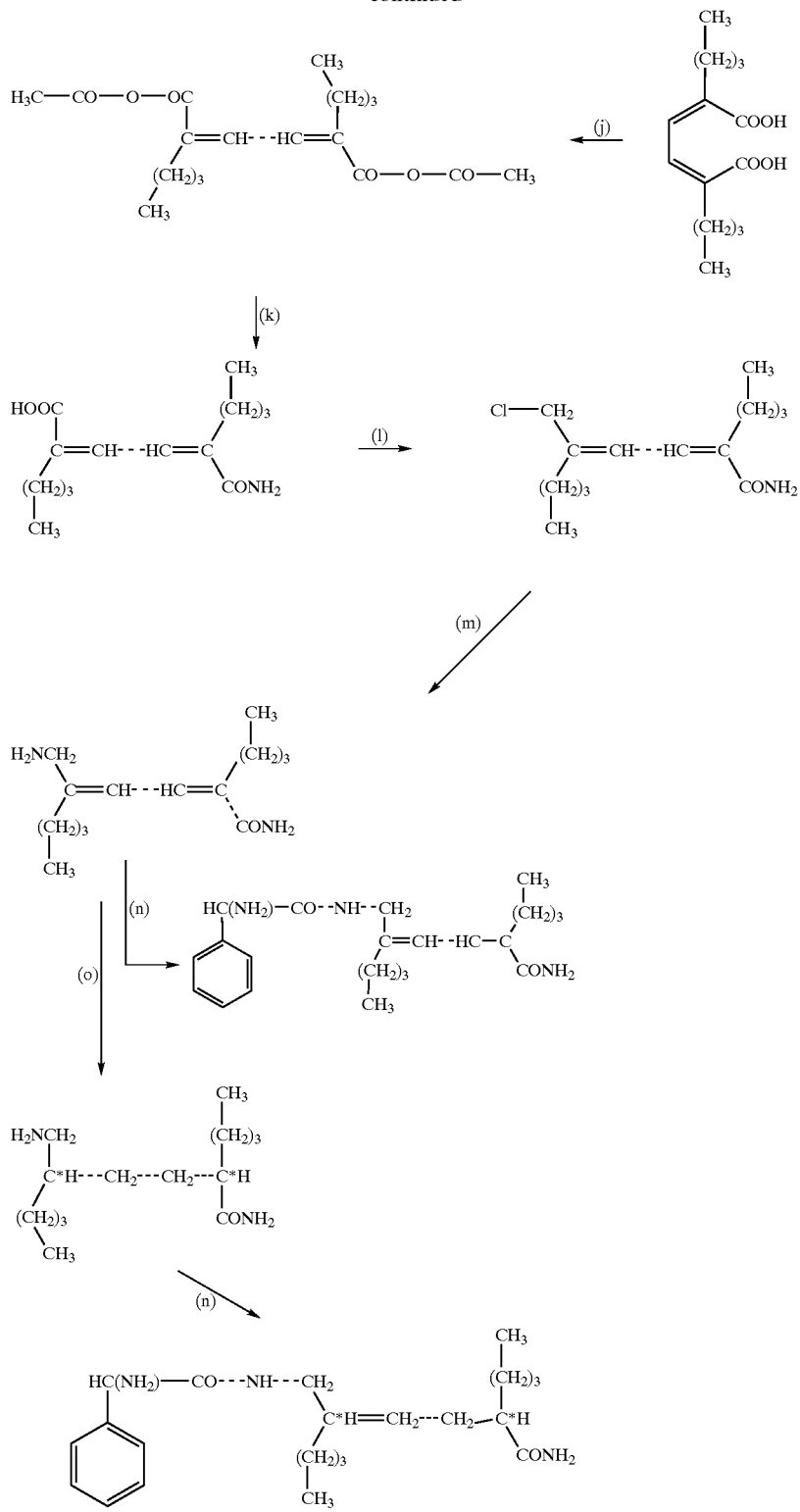

The foregoing may be understood better from the following examples that are presented for the purposes of illustration and are not intended to limit the scope of the invention. In these examples, the individual reactions being illustrated, in (Scheme One, Two and Three), are indicated by a bracketed letter, such as for example "(a)".

EXAMPLE 1

A. Synthesis of N-(trans,trans-2,4-pentadiene-2,5-di-n-butyl-5-carboxamide)-L-phenyl glycinamide Reaction (a): Synthesis of n-butyrophenone. (Friedel-Crafts Reaction). 0.1 Mole (10.7 gm.) of n-butyryl chloride, 0.2 mole (16 gm.) of benzene, and 0.2 mole (27 gm.) of anhydrous $AlCl_3$ are added to 100 ml of nitrobenzene, and the mixture heated under reflux for 2 hours. The mixture is then cooled, acidified with conc. HCl, diluted with 200 ml distilled water and steam distilled. The aqueous phase of the distillate is discarded, and the organic phase is dried with anhyrous $Na_2SO_4$. The solvents are then removed by distillation, and the residue of n-butyrophenone is used without further purification.

Reaction (b): Synthesis of n-butylbenzene. (Wolff-Kischner Reduction). The product from Reaction (a) is mixed with 200 ml of ethylene glycol, 10 gm. of KOH and 0.15 mole (5 gm.) of hydrazine. The mixture is heated to reflux temperature while being stirred, and the water evolved is collected. When the evolution of water ceases, the mixture is cooled, diluted with 200 ml of distilled water, and steam distilled. The distillate is extracted three times with 100 ml portions of benzene, and after the combined extracts are dried over anhydrous $Na_2SO_4$, the benzene is removed by distillation. The product, n-butylbenzene, is crystallized from absolute ethanol: m.p. 88° C.

Reaction (c): Synthesis of para-n-butylbutyrophenone. Reaction (a) is repeated using 0.1 mole (13.4 gm.) of n-butyl benzene, prepared in Reaction (b) supra and 0.1 mole (10.7 gm.) of n-butyryl chloride. The crude reaction product is isolated as is the product in Reaction (a).

Reaction (d): Synthesis of 1,4-di-n-butylbenzene. Reaction (b) is repeated using the approximately 0.1 mole of product from Reaction (c) as the starting material. The reaction product, 1,4-di-n-butylbenzene, is crystallized from absolute ethanol, and the structure confirmed by NMR spectroscopsy.

Reaction (e): Synthesis of 2,5-di-n-butyl-nitrobenzene. 0.1 Mole (19.1 gm.) of 1,4-di-n-butylbenzene prepared in Reaction (d) is dissolved in 60 ml of a 1:2 (v:v) mixture of conc. $HNO_3$ and conc. $H_2SO_4$. The solution is stirred, while its temperature is maintained at 90° C., for one hour. The solution becomes yellow indicating that the reaction has occurred. The product is not isolated.

Reaction (f): Synthesis of 2,5-di-n-butylaniline. To the reaction mixture from Reaction (e) 0.4 mole (26 gm.) of powdered zinc is slowly added while the stirring is continued. The yellow color fades as the reaction comes to completion. The reaction mixture is cooled, diluted with 400 ml of distilled water, and the acid content neutralized by the addition of an excess of 10 M NaOH. The reaction product is extracted into diethyl ether, and the combined ether extracts are washed with distilled water. From the ether solution, the hydrochloride of the reaction product slowly precipitates after the addition of 10 ml of conc. HCl and by chilling the mixture. The recovered product is pure 2,5-di-n-butylaniline hydrochloride as indicated by GLC of the free base.

Reaction (g): Synthesis of 2,5-di-n-butylbenzene diazonium salt. 0.1 Mole (24.0 gm.) of 2,5-di-n-butylaniline hydrochloride prepared in Reaction (f) is dissolved in 130 ml 3 M $H_2SO_4$ and the mixture cooled to 0° C. by surrounding it with crushed ice. To the chilled solution, 0.12 mole of $NaNO_2$ (8.3 gm.) is slowly added with stirring which is continued until starch-iodide paper turns blue.

Reaction (h): Synthesis of 2,5-di-n-butylphenol. The solution from Reaction (g) is diluted with an equal volume of distilled water so as to adjust the $H_2SO_4$ concentration to approximately 1.5 M, and this solution is heated under reflux for 2 hours. The 2,5-di-n-butylphenol thus formed is removed from this reaction mixture by steam distillation and is extracted from the distillate with benzene. The benzene is distilled, and the residue analyzed by GLC and GLC-MS.

Reaction (i): Synthesis of cis 1,3-butadiene-1,4-di-n-butyl-1,4-dicarboxylic grid. 0.33 Mole of peracetic acid (63 gm., 56 ml of 40% peracetic acid) is added to a 250 ml, two necked reaction flask fitted with a condenser, a dropping funnel and a magnetic stirrer. The flask is immersed in a water bath maintained at 25°–30° C. While the peracetic acid is being stirred, a cold solution of 2,5-di-n-butylphenol (0.1 mole, 20.6 gm.) from Reaction (h) in 75 ml of glacial acetic acid is added dropwise over a period of 4 hours. The temperature of the reaction mixture is maintained between 30°–35° C. Solid material begins to separate from the solution and when the addition of the phenol is complete, the mixture is stirred for 1 hour and then allowed to stand for 8 hours while its temperature is kept below 40° C. Then, after the mixture has remained at room temperature for 4 days, the crude product is obtained by suction filtration.

Reaction (j): Synthesis of mixed acetyl anhydrides of trans,trans-1,3-butadiene-1,4-di-n-butyl-1,4-dicarboxylic acid. The product obtained in Reaction (i) is dissolved in 50 ml of acetic anhydride with heating and stirring and to this solution is added 0.25 mole (20 gm.) of acetyl chloride. The temperature of this stirred solution is maintained at 100° C. under reflux conditions until hydrogen chloride is no longer evolved. Under these conditions, the cis,cis-isomer is converted to the trans,trans-isomer, and the double anhydride is formed. After the mixture has cooled, it is lyophilized to dryness.

Reaction (k): Synthesis of trans,trans-1,3-butadiene-1,4-di-n-butyl-1-carboxyl-4-carboxamide. The crude product of Reaction (j) is dissolved in 200 ml of anhydrous ammonia in a Dewar flask and the excess ammonia is allowed to evaporate. The residue consists of a mixture of ammonium dicarboxylate, diamide, monoamide-mono ammonium carboxylate, acetamide and ammonium acetate and is dissolved in hot water. This solution is poured onto a 5.0×100 cm. column of anion exchange resin in the acetate form maintained at 100° C. Hot water and then hot 0.01 M NaCl is used to elute the adsorbed materials. The order of elution is monitored by determination of the pH of successive 25 ml fractions of eluate. The desired substance, trans,trans-1,3-butadiene-1,4-di-n-butyl-1-carboxyl-4-carboxamide is the second material to be eluted by the 0.01 NaCl. The fractions of eluate which contain this material as the sodium salt, are combined and, after passage through a cation-exchange column in the hydrogen form, are lyophilized to dryness. The dicarboxylate and diamide forms of the starting material obtained from the anion exchange column are reworked to increase the yield of the desired product.

If monomethylamine and dimethylamine are used separately in the above synthesis instead of ammonia, the monomethyl and dimethyl carboxamides, respectively, can be synthesized.

Reaction (l): Synthesis of trans,trans-1,3-butadiene-1,4-di-n-butyl-1-chloromethyl-4-carboxamide. 0.1 Mole of the product of Reaction (k) is dissolved in chloroform and 0.11 mole (4.6 gm.) of diazomethane ($CH_2N_2$) in chloroform is added. The yellow color of the diazomethane quickly fades, indicating that the methyl ester has formed. Excess diazomethane is removed by the addition of a few drops of glacial acetic acid to form methyl acetate.

The chloroform is removed by distillation to dryness, and the residue is dissolved in absolute ethanol. 0.50 Mole of sodium beads is added to this solution, and after the evolution of hydrogen subsides, the solution is diluted with distilled water and extracted exhaustively with methylene chloride. The combined extracts are dried with anhydrous $Na_2SO_4$, and the volume is reduced by distillation to about 100 ml.

To this solution of trans,trans-1,3-butadiene-1,4-di-n-butyl-1-hydroxymethyl-4-carboxamide thus obtained, 0.1 mole of thionyl chloride ($SOCl_2$, 8 gm.) is added, and the solution is heated under reflux until the evolution of $SO_2$ and hydrogen chloride ceases. The target product is obtained as the residue by evaporating the solution to dryness.

Reaction (m): Synthesis of trans,trans-1,3-butadiene-1,4-di-n-butyl-1-aminomethyl-4-carboxamide. (Gabriel Synthesis). 0.1 Mole (26.8 gm.) of the product from Reaction (1) is dissolved in 200 ml of dimethylformamide and 0.1 mole (18.5 gm.) of potassium phthalimide is then added. The mixture is stirred and warmed to between 300 and 50° C. for one hour. After the formed KCl is removed by filtration, 0.5 mole (16 gm.) of hydrazine, together with sufficient 95% ethanol to form a solution, is added and the solution refluxed for 2 hours. The reaction mixture is cooled, diluted generously with distilled water, and extracted exhaustively with 50 ml portions of toluene. 15 ML of conc. HCl are added to the combined toluene extracts, the combination thoroughly mixed, and allowed to stand at 5° C. The hydrochloride of the named product forms slowly, is isolated by filtration, and is twice recrystallised by repeating the process of forming the hydrochloride. It is characterized and its structure confirmed by NMR spectroscopy of the free base.

If the chloromethyl compound used in this synthesis is condensed with methylamine, instead of undergoing the Gabriel Synthesis with potassium phthalimide, the methylamino compound can be obtained.

Reaction (n): Synthesis of N-(2,5-di-n-butyl-4-trans,trans-pentadiene-5-carboxamide)-L-phenylglycinamide (the named trans,trans-1,3-butadiene based compound of the above Formula). 0.12 Mole of each of the commercial available compounds, benzylchloroformate (20.5 gm.) and L-phenylglycine (18.1 gm.), are dissolved in 200 ml of acetonitrile and heated under reflux for 1 hour to form 0.11 mole, i.e. 90% yield, of carbobenzyloxy ("CBZ") L-phenylglycine. To this solution is added 0.23 mole (20 gm.) of triethylamine, 0.1 mole (10.9 gm.) of ethylchloroformate and 50 ml of acetonitrile. Heating under reflux is continued for another hour, and then the solution is distilled to dryness. The residue which contains the mixed anhydride, $CBZ-NH-CH(C_6H_5)-COO-COOC_2H_5$ (approximately 0.1 mole) is dissolved in 200 ml of toluene. This solution is washed three times with 50 ml of distilled water and dried with anhydrous $Na_2SO_4$.

To the resulting toluene solution of the mixed anhydride is added a toluene solution of 0.1 mole of the trans,trans-1,3-butadiene-1,4-di-n-butyl-1-aminomethyl-4-carboxamide prepared in Reaction (m). The resulting solution is heated at 100° C. and stirred until the evolution of $CO_2$ ceases indicating that the substituted amide of CBZ-L-phenylglycine has formed. The toluene is then removed from the reaction mixture by distillation in vacuo, and the residue is dissolved in liquid ammonia in a Dewar flask. To this solution 4.6 gm. of sodium beads are added, and the ammonia is allowed to evaporate. The residue is taken up in the minimum volume of boiling glacial acetic acid from which the named product crystallized and is recovered by filtration. It is washed with small volumes of cold glacial acetic acid, air dried, and characterized by infra red and NMR spectroscosopy (X=trans, trans >C=CH—HC=C<, $R_1$=H, $R_2$=H, $R_3$=n-butyl, $R_4$=n-butyl, $R_5$=H, $R_6$=$R_7$—(C)$_n$—HC(NH)—CO—, where $R_7$=phenyl, n=0).

Reaction (o): Synthesis of 5-aminomethyl-8-dodecane carboxamide (the perhydro-1,3-butadiene-based intermediate). 0.1 Mole (23.8 gm.) of trans,trans-1,3-butadiene-1,4-di-n-butyl-1-aminomethyl-4-carboxamide from Reaction (m) is dissolved in the minimum volume of 95% ethanol and subjected, with shaking, to hydrogen gas at atmospheric pressure in the presence of 50 mg. of Adams platinum oxide catalyst. The reduction is quantitative as reflected by the volume of hydrogen consumed (0.2 mole). The product has two chiral centers, and thus the residue obtained by evaporation of the solvent contained a mixture of four optical isomers. The isomers in this racemic mixture can be separated by fractional crystallization after they have been converted to their diastereometric salts with (+)-tartaric acid.

This mixture is converted to the racemic mixture of the four possible optical isomers of N-(5-methylene-8-dodecane carboxamide)-L-phenylglycinamide by repetition of Reaction (n) (X=>C*H(CH$_2$)$_2$HC*<, $R_1$=H, $R_2$=H, $R_3$=n-butyl, $R_4$=n-butyl, $R_5$=H, $R_6$=$R_7$—(CH$_2$)$_n$—HC(NH$_2$)—CO—, where $R_7$=phenyl, n=0).

The specific L-, D-isomer (amino acid convention) can be obtained after resolving the mixture of four isomers produced supra.

Reactions Sequence for the Synthesis of the trans Ethylene Based Compounds of the Formula Scheme Two

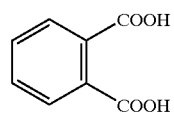 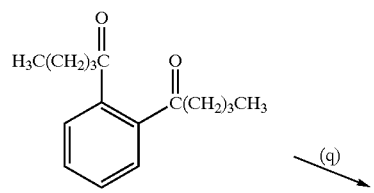

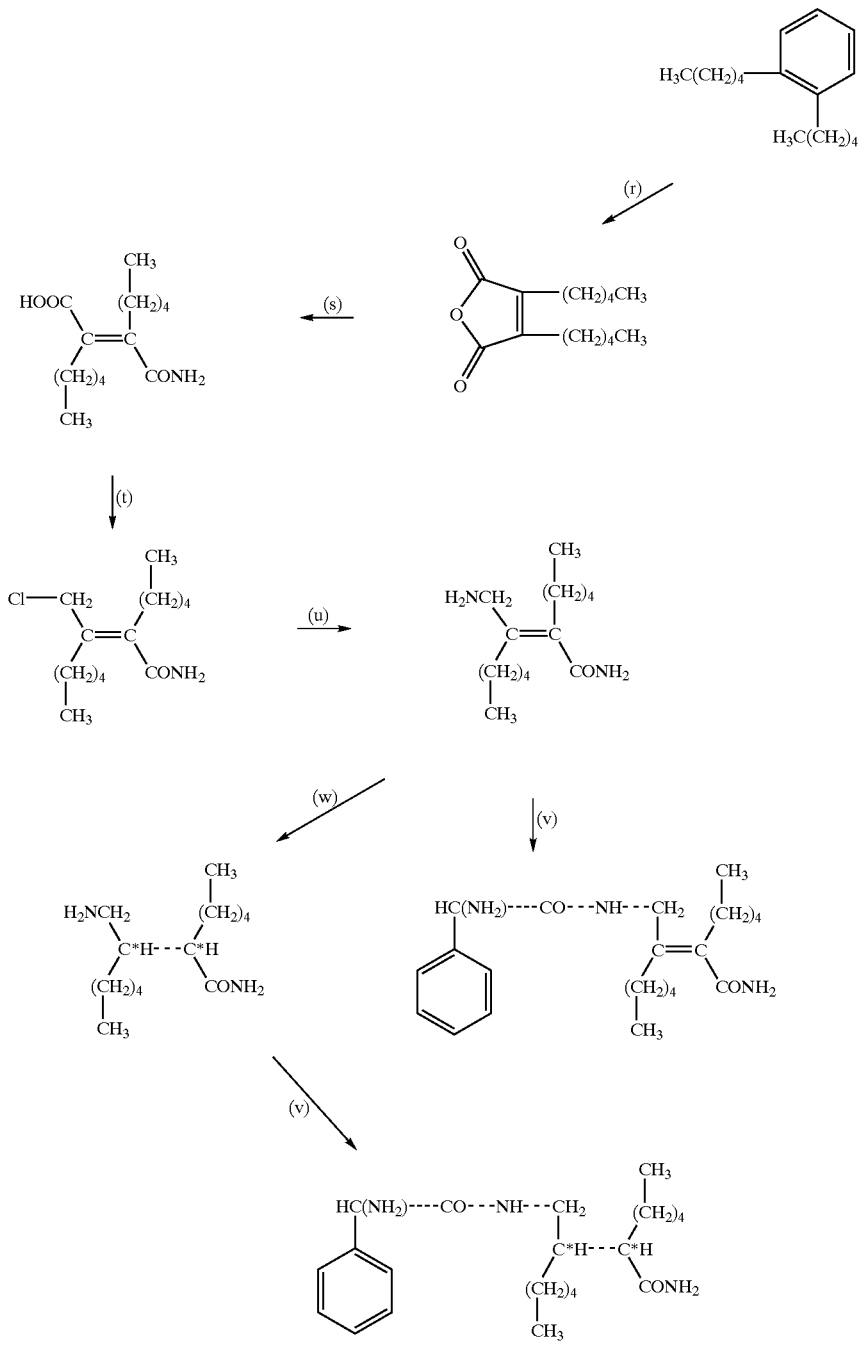

EXAMPLE 2

B. Synthesis of N-(trans-2,3-di-n-amyl-2-butenoic acid amide)-L-phenylglycinamide Reaction (p): Synthesis of ortho-dipentanoylbenzene. 0.1 Mole (16.6 gm.) of phthalic acid is dissolved in 100 ml of benzene and 0.2 mole (23.6 gm.) of thionyl chloride is added slowly while the solution is stirred. It is then heated under reflux until the evolution of $SO_2$ and hydrogen chloride ceases.

Into a two-necked, 1 liter flask, fitted with a condenser, dropping funnel and magnetic stirrer, is added 200 ml of anhydrous diethyl ether. The condenser is closed with a calcium chloride drying tube filled with anhydrous calcium chloride and 0.2 mole (4.8 gm.) of clean, dry magnesium ribbon, cut into 1 cm. lengths, is added to the flask. While the mixture is stirred rapidly, 0.2 mole (18.5 gm.) of n-butyl chloride in 50 ml. of anhydrous diethyl ether is added dropwise so as to control the reaction. When all of the magnesium has reacted, 0.2 mole (9.6 gm.) of anhydrous $CaCl_2$ in anhydrous diethyl ether is slowly added to the flask.

After this addition, the temperature of the reaction mixture is reduced to −20° C. and the solution of phthalyl chloride, prepared supra, is slowly added. Stirring is continued for another hour, and then 200 ml of saturated ammonium chloride is slowly added. When all of the materials have dissolved, the temperature of the mixture is allowed to return to room temperature, the aqueous phase is removed, and the organic phase is distilled to dryness. The residue contains the named product.

Reaction (q): Synthesis of ortho-di-n-amylbenzene. (Wolff-Kischner Reduction). The residue from Reaction (p) is suspended in 200 ml of ethylene glycol, and 10 gms. each of KOH and hydrazine are added. The procedure of Reaction (d), Scheme One, supra is then continued, and the structure of the product obtained is that of the expected compound.

Reaction (r): Synthesis of di-n-amyl maleic anhydride. The ortho-di-n-amylbenzene prepared in Reaction (q) is dissolved in cyclohexane and placed in a glass "trap" so that a rapid stream of warm air can be passed, in the reverse direction, through the solution. The aerosol thus formed is passed through a thick-walled, glass U-tube filled with $V_2O_5$ and immersed in a bath of molten Woods metal at 450° C. The product, di-n-amyl maleic anhydride, is collected by passing the effluent air stream through a trap surrounded by circulating water at 5° C.

Reaction (s): Synthesis of trans 1,2-di-n-amyl ethylene-1-carboxyl-2-carboxamide. The product of Reaction (r) is dissolved in the minimum volume of benzene, and the solution slowly added to 50 ml of liquid ammonia in a Dewar flask. The mixture is gently stirred as the ammonia evaporates, and the residual benzene solution is transferred to a separatory funnel with additional benzene. A few crystals of iodine are added, and the solution thoroughly mixed. After the mixture has remained overnight at room temperature, it is washed twice with 100 ml portions of 1 M HCl and twice with distilled water. After the benzene solution is dried over anhydrous $Na_2SO_4$, it is distilled to dryness. The residue containes the named product.

Reaction (t): Synthesis of trans 2,3-di-n-amyl-1-chloro-2-butenoic acid amide. The product from Reaction (s) is dissolved in 100 ml of chloroform and 0.1 mole (4.2 gm.) of diazomethane ($CH_2N_2$), prepared in 50 ml of chloroform, is added. When the reaction is completed as indicated by the cessation of fading of the yellow color, the solution is evaporated to dryness. The methyl ester residue is dissolved in absolute ethanol and 0.3 mole (7.0 gm.) of sodium beads is added. After the reaction ceases, the solution is reduced to dryness and the residue, which contains trans-2,3-di-n-amyl-1-hydroxy-2-butenoic acid amide, is dissolved in 100 ml of benzene. To this solution 0.1 mole (12 gm.) of thionyl chloride is added, and the solution refluxed gently until the evolution of $SO_2$ and hydrogen chloride ceases. The residue obtained by distilling the benzene solution to dryness contains the named product.

Reaction (u): Synthesis of trans 2,3-di-n-amyl-1-amino-2-butenoic acid amide. (Gabriel Synthesis). 0.1 Mole of product from Reaction (t) is reacted with potassium phthalimide as described in Reaction (m), Scheme One, supra to form the named compound.

If the chloro compound prepared Reaction (t) is reacted with monomethyl amine instead of undergoing the Gabriel Synthesis, the N-methyl analogue of the product of Reaction (u) is obtained.

Reaction (v): Synthesis of N-(trans 2,3-di-n-amyl-2-butenoic acid amide)-L-phenylglycinamide. (A trans-ethylene-based compound of the above Formula). This target compound is synthesized by condensing the 1-amino compound formed in Reaction (u) with L-phenylglycine as described in Reaction (n), Scheme One, supra. (X=trans >C=C<, $R_1$=H, $R_2$=H, $R_3$=n-amyl, $R_4$=n-amyl, $R_5$=H, $R_6$=$R_7$—$(CH_2)_n$—HC($NH_2$)—CO—, where $R_7$=phenyl, n=0).

Reaction (w): Synthesis of 6-aminomethyl-7-dodecane carboxamide. This compound is synthesized by subjecting the aminomethyl compound formed in Reaction (u) supra to catalytic hydrogenation as described in Reaction (o), Scheme One, supra. This compound has two chiral centers, and thus the product of this synthesis is a racemic mixture of four optical isomers. These isomers can be separated by fractional crystallization after their conversion to diastereometric salts by reaction with (+)-tartaric acid.

This mixture of isomers is converted to the mixture of the four possible optical isomers of N-(6-methylene-7-dodecane carboxamide)-L-phenylglycinamide by repeating Reaction (n), Scheme One, supra. (X=>*CHHC*<, $R_1$=H, $R_2$=H, $R_3$=n-amyl, $R_4$=n-amyl, $R_5$=H, $R_6$=$R_7$—$(CH_2)_n$—HC($NH_2$)—CO—, where $R_7$=phenyl, n=0)

The specific L-,D-isomer (amino acid convention) can be obtained by resolving, as indicated supra, the mixture of four isomers produced by catalytic hydrogenation supra.

Reaction Sequence for the Synthesis of 1,3-Substituted Propane-Based Compounds of Formula I

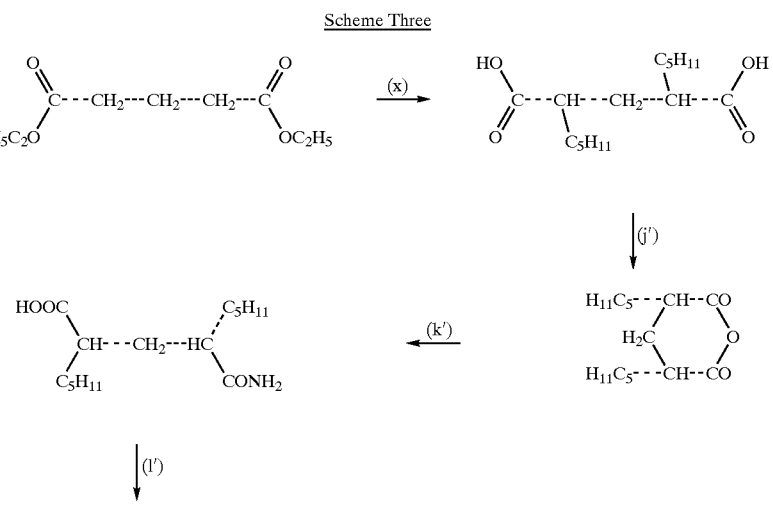

Scheme Three

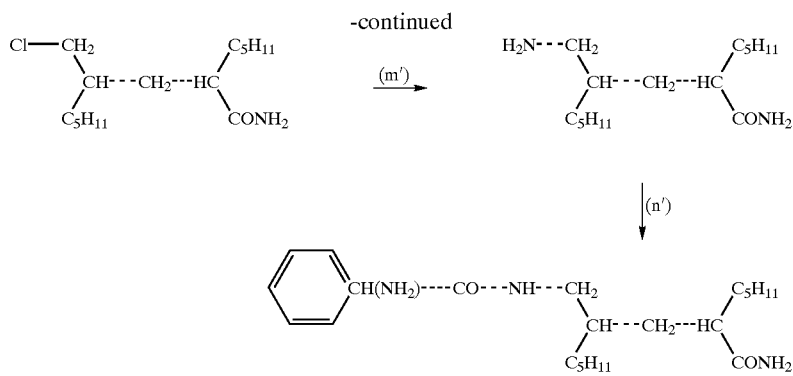

EXAMPLE 3

C. Synthesis of N-(2,4-di-amylpentanoic acid amide)-L-phenylglycinamide

Reaction (x): Synthesis of 2,4-di-n-amylglutaric acid (Malonic Ester Synthesis). 0.3 Mole (6.9 gm.) of sodium beads is slowly added, with magnetic stirring, to 300 mL. of absolute ethanol. When the evolution of hydrogen gas has ceased, 0.1 mole (18.8 gm.) of diethylglutaric acid is dissolved in the mixture. The stirring is continued, and the mixture is heatet to reflux while 0.2 mole (30.2 gm.) of n-amyl bromide is slowly added dropwise. When the formation of sodium bromide has ceased, the mixture is concentrated under reduced pressure to about 100 mL. 200 mL. of 1.5 molar hydrochloric acid is then added, and the mixture is heated under reflux for two hours, diluted with 500 mL. of distilled water, transferred to a separatory funnel, and extracted four times with 100 mL. portions of diethyl ether. The combined ether extracts are distilled to dryness in a tared distillation flask and the crude residue of 2,4-di-n-amylglutaric acid is weighed.

Reaction (j~): Synthesis of 2,4-di-n-amylglutaric acid anhydride. 30 gm. of the residue from Reaction (x) supra is heated as described in Reaction (j), Scheme One, supra to produce a quantitative yield of the targeted anhydride product.

Reaction (k~): Synthesis of 2-n-amyl-4-carboxy-4-nonanoic acid amide. 25 gm. of the product from Reaction (j~) above is treated with anhydrous ammonia as in Reaction (k), Scheme One, supra to yield the desired product which, in this case, does not require purification by chromatography. If monomethylamine and dimethylamine are used separately instead of ammonia in this synthesis, the monomethyl and dimethyl carboxamides, respectively, can be synthesized.

Reaction (l~): Synthesis of 2-n-amyl-4-chloromethyl nonanoic acid amide. The product from Reaction (k~) above is treated with diazomethane, sodium beads plus absolute ethanol, and thionyl chloride as in Reaction (l) Scheme One, supra to yield the desired product.

Reaction (m~): Synthesis of 2-n-amyl-4-aminomethyl-nonanoic acid amide. (Gabriel Synthesis). 0.1 Mole (27.6 gm.) of product from Reaction (l~) above is treated as in Reaction (l), Scheme One supra to yield the pure hydrochloride of the desired compound. If the chloromethyl compound used in this reaction is condensed with N-methylphthalimide, rather than with phthalimide, the methyl amino derivative of the desired compound can be synthesized.

Reaction (n~): Synthesis of N-(2,4-di-n-amylpentanoic acid amide)-L-phenylglycinamide (the named 1,3-disubstituted propane based compound of the Formula). 0.1 Mole (25.6 gm.) of the pure product from Reaction (m~) above is treated as in Reaction (m), Scheme One, supra. The product is characterized by infra red and NMR spectroscopy. It is a racemic mixture of the four possible optical isomers from which the specific L-,D-isomer (amino acid convention) can be obtained by fractional crystallization of the diastereometric salts with (+)-tartaric acid. (X=>C*H—CH$_2$—HC*< where "*" represents a chiral carbon, $R_1$=H, $R_2$=H, $R_3$=n-amyl, $R_4$=n-amyl, $R_5$=H, $R_6$=$R_7$—(CH$_2$)$_n$—HC(NH$_2$)—CO—, where $R_7$=phenyl, n=0.

The four different structural features indicated by the "X" of the above Formula (i.e., each arm of the "X" representing a bond of the selected structural feature) represent the ways by means of which these compounds can acquire essentially the same hydrophobic surface which involves about 12 methylene groups linearly arranged. Thus, even though these four structural features provide, strictly speaking, for four different chemical compounds, the hydrophobisities of the four molecules are essentially identical. This structural aspect is preferable for the biological activity of the compounds of the above Formula.

An in vitro biological assay of the activities of compounds of this invention and their synthesis intermediates can be conducted by employing normal human erythrocytes in which the magnesium binding defect is created by incubating these thoroughly saline-washed cells at 5° C. in Alsevers solution; the mixture has a hematocrit of 50% and contains 1.25 mg. of sodium deoxycholate per ml.

After 72 hours of incubation, the magnesium binding defect is present in the cell membranes of these erythrocytes as evidenced by their decreased magnesium content when compared with the magnesium content of plasma membranes from control erythrocytes which are identical in all respects except that they have been similarly incubated in Alsevers solution only, i.e. the positive control.

Biological activity can be determined by measuring the magnesium contents of the plasma membranes of thoroughly washed, depleted erythrocytes prepared supra which have been incubated at 37° C. for three hours in Krebs-Ringer phosphate solutions to which the test compound has and has not been added. The mixture having cells, Krebs-Ringer solution and no test compound is the negative control, and the magnesium content of the plasma membranes of the contained cells must be significantly less than that of undepleted cells incubated in magnesium-free Krebs-Ringer solution. Positive biological activity is indicated when the magnesium content of the plasma membranes of the depleted erythrocytes which are incubated in Krebs-Ringer solution containing the test compound is significantly higher than that of the negative control and may be the same as, or greater than, that of the positive control.

The compounds of the above Formula are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well-known in the pharmaceutical art and are comprised of at least one active compound.

The present invention also includes pharmaceutical compositions which contain, as the active ingredient, the compounds of the above Formula associated with pharmaceutically acceptable carriers. In making the compositions of the present invention, the active ingredient is usually mixed with an excipient, diluted by an excipient or enclosed within such a carrier which can be in the form of a capsule, sachet, paper or other container. When the incipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoate; sweetning agents; and flavoring agents. The compositions of the invention can be formulated, by employing procedures known in the art, so as to provide quick, sustained or delayed release of the active ingredient after administration to the patient.

The compositions are preferably formulated in a unit dosage form, each dosage containing from about 0.05 to about 100 mg, but usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For example, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way.

In some instances dosage levels below the lower limit of the aforesaid range may be more than adequate, while in other cases still larger doses may be employed without causing any harmful side effects, provided that such large doses are first divided into several smaller doses for administration throughout the day.

Other products of the teaching of this invention will be readily apparent to those skilled in the art, and such products also fall within the scope of the invention. Thus the invention is based on the discovery of the association of certain human diseases, such as "salt-sensitive" essential hypertension, Type 2 diabetes mellitus, pre-eclampsia and eclampsia, with the presence of the magnesium binding defect in the plasma membranes of the somatic cells of such patients, and the efficacy of the pentapeptide, and its included C-terminal tetrapeptide, at the C-terminal end of the mammalian tachykinins, e.g., Substance P, to correct the binding defect and thus to ameliorate and/or to prevent the disease.

It will of course be understood that the present invention has been described supra purely by way of example, and modifications of detail can be made within the scope of the invention.

I claim:

1. A compound of the formula:

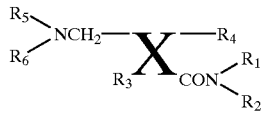

wherein:

$R_1$, $R_2$ and $R_5$ are independently selected from the group consisting of H and $C_1$–$C_2$ alkyl;

$R_3$ and $R_4$ are selected from $C_2$–$C_8$ alkyl;

$R_6$ is selected from the group consisting of H and the L-isomer (amino acid convention) of $R_7$—$(CH_2)_n$—$HC(NH_2)$—CO—;

wherein n is an integer from 0 to 3;

$R_7$ is selected from the group consisting of $C_3$–$C_6$ alkyl and unsubstituted aryl wherein said unsubstituted aryl is independently selected in each instance from the group consisting of phenyl, biphenyl, and naphthyl;

X is independently selected in each instance from the group consisting of trans, trans >C=CH—HC=C<, trans >C=C<, and >C*H—$(CH_2)_m$—HC*<, where "*" indicates a chiral carbon atom and $R_3$ and $R_4$ are oriented L- and D-(amino acid convention) at these respective chiral centers; and m=0, 1 or 2, or a pharmaceutically acceptable salt, solvate or prodrug thereof.

2. The compound of claim 1 wherein X is selected from trans, trans <CH=CH—HC=C< or trans >C=C<.

3. The compound of claim 2 wherein $R_1$, $R_2$ and $R_5$ are hydrogen.

4. The compound of claim 3 wherein $R_6$ is L-phenylglycine or L-valine.

5. The compound of claim 4 wherein $R_1$ is methyl and $R_2$ and $R_5$ are hydrogen.

6. The compound of claim 4 wherein $R_1$ and $R_2$ are methyl and $R_5$ is hydrogen.

7. The compound of claim 4 wherein $R_1$ and $R_2$ are hydrogen and $R_5$ is methyl.

8. The compound of claim 4 wherein $R_1$, $R_2$ and $R_5$ are methyl.

9. The compound of claim 3 wherein $R_6$ is L-4-hydroxyphenylglycine or L-leucine.

10. The compound of claim 9 wherein $R_1$ is methyl and $R_2$ and $R_5$ are hydrogen.

11. The compound of claim 9 wherein $R_1$ and $R_2$ are methyl and $R_5$ is hydrogen.

12. The compound of claim 9 wherein $R_1$ and $R_2$ are hydrogen and $R_5$ is methyl.

13. The compound of claim 9 wherein $R_1$, $R_2$ and $R_5$ are methyl.

14. The compound of claim 3 wherein $R_6$ is L-(1 or 2)-naphthylglycine or L-isoleucine.

15. The compound of claim 14 wherein $R_1$ is methyl and $R_2$ and $R_5$ are hydrogen.

16. The compound of claim 14 wherein $R_1$ and $R_2$ are methyl and $R_5$ is hydrogen.

17. The compound of claim 14 wherein $R_1$ and $R_2$ are hydrogen and $R_5$ is methyl.

18. The compound of claim 14 wherein $R_1$, $R_2$ and $R_5$ are methyl.

19. The compound of claim 3 wherein $R_6$ is L-biphenylglycine or L-norleucine.

20. The compound of claim 19 wherein $R_1$ is methyl and $R_2$ and $R_5$ are hydrogen.

21. The compound of claim 19 wherein $R_1$ and $R_2$ are methyl and $R_5$ is hydrogen.

22. The compound of claim 19 wherein $R_1$ and $R_2$ hydrogen and $R_5$ is methyl.

23. The compound of claim 19 wherein $R_1$, $R_2$ and $R_5$ are methyl.

24. The compound of claim 1 wherein X is either $>C^*H—(CH_2)_2—HC^*<$, or $>C^*H—HC^*<$.

25. The compound of claim 24 wherein $R_1$, $R_2$ and $R_5$ are hydrogen.

26. The compound of claim 25 wherein $R_6$ is L-phenylglycine or L-valine.

27. The compound of claim 26 wherein $R_1$ is methyl and $R_2$ and $R_5$ are hydrogen.

28. The compound of claim 26 wherein $R_1$ and $R_2$ are methyl and $R_5$ is hydrogen.

29. The compound of claim 26 wherein $R_1$ and $R_2$ are hydrogen and $R_5$ is methyl.

30. The compound of claim 26 wherein $R_1$, $R_2$ and $R_5$ are methyl.

31. The compound of claim 24 wherein $R_6$ is L-4-hydroxyphenylglycine or L-leucine.

32. The compound of claim 31 wherein $R_1$ is methyl and $R_2$ and $R_5$ are hydrogen.

33. The compound of claim 31 wherein $R_1$ and $R_2$ are methyl and $R_5$ is hydrogen.

34. The compound of claim 31 wherein $R_1$ and $R_2$ are hydrogen and $R_5$ is methyl.

35. The compound of claim 31 wherein $R_1$, $R_2$ and $R_5$ are methyl.

36. The compound of claim 25 wherein $R_6$ is L-(1 or 2)-naphthylglycine or L-isoleucine.

37. The compound of claim 36 wherein $R_1$ is methyl and $R_2$ and $R_5$ are hydrogen.

38. The compound of claim 36 wherein $R_1$ and $R_2$ are methyl, and $R_5$ is hydrogen.

39. The compound of claim 36 wherein $R_1$ and $R_2$ are hydrogen and $R_5$ is methyl.

40. The compound of claim 36 wherein $R_1$, $R_2$ and $R_5$ are methyl.

41. The compound of claim 25 wherein $R_6$ is L-biphenylglycine or L-norleucine.

42. The compound of claim 41 wherein $R_1$ is methyl and $R_2$ and $R_5$ are hydrogen.

43. The compound of claim 41 wherein $R_1$ and $R_2$ are methyl and $R_5$ is hydrogen.

44. The compound of claim 41 wherein $R_1$ and $R_2$ are hydrogen and $R_5$ is methyl.

45. The compound of claim 41 wherein $R_1$, $R_2$ and $R_5$ are methyl.

46. The compound of claim 3 wherein $R_6$ is hydrogen.

47. The compound of claim 46 wherein $R_1$ is methyl and $R_2$ and $R_5$ are hydrogen.

48. The compound of claim 46 wherein $R_1$ and $R_2$ are methyl and $R_5$ is hydrogen.

49. The compound of claim 46 wherein $R_1$ and $R_2$ are hydrogen and $R_5$ is methyl.

50. The compound of claim 46 wherein $R_1$, $R_2$ and $R_5$ are methyl.

51. The compound of claim 25 wherein $R_6$ is hydrogen.

52. The compound of claim 51 wherein $R_1$ is methyl and $R_2$ and $R_5$ are hydrogen.

53. The compound of claim 51 wherein $R_1$ and $R_2$ are methyl and $R_5$ is hydrogen.

54. The compound of claim 51 wherein $R_1$ and $R_2$ are hydrogen and $R_5$ is methyl.

55. The compound of claim 51 wherein $R_1$, $R_2$ and $R_5$ are methyl.

56. A pharmaceutical composition comprising a pharmaceutically acceptable carrier and a compound of the formula:

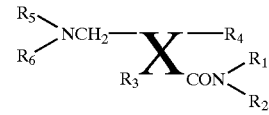

wherein:

$R_1$, $R_2$ and $R_5$ are independently selected from the group consisting of H and $C_1$–$C_2$ alkyl;

$R_3$ and $R_4$ are selected from $C_2$–$C_8$ alkyl;

$R_6$ is selected from H and the L-isomer (amino acid convention) of $R_7$—$(CH_2)_n$—$HC(NH_2)$—$CO$—;

wherein n is an integer from 0 to 3;

$R_7$ is selected from the group consisting of $C_3$–$C_6$ alkyl and unsubstituted aryl, wherein said unsubstituted aryl is independently selected in each instance from the group consisting of phenyl, biphenyl, and naphthyl;

X is independently selected in each instance from the group consisting of trans, trans $>C=CH—HC=C<$, trans $>C=C<$, and $>C^*H—(CH_2)_m—HC^*<$ where "*" indicates a chiral carbon atom and $R_3$ and $R_4$ are oriented L- and D-(amino acid convention) at these respective chiral centers; and m=0, 1 or 2, or a pharmaceutically acceptable salt, solvate or prodrug thereof.

57. The pharmaceutical composition of claim 56 wherein $R_1$, $R_2$ and $R_5$ are H;

$R_3$ and $R_4$ are independently selected from the group consisting of n-butyl, n-amyl and n-hexyl;

$R_6$ is selected from the group consisting of L-phenylglycine and L-valine; and X is selected from the group consisting of trans,trans $>C=CH—HC=C<$, trans $>C=C<$, $>C^*H—(CH_2)_2—C^*H<$, and $>C^*H—H^*C<$ (wherein the "*" indicates a chiral carbon).

58. A method of treating a mammal affected with the magnesium-binding defect, comprising administering to the mammal a pharmaceutically effective amount of a compound of the formula:

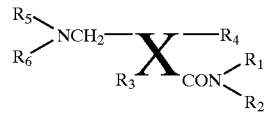

wherein:
$R_1$, $R_2$ and $R_5$ are independently selected from the group consisting of H and $C_1$–$C_2$ alkyl;
$R_3$ and $R_4$ are selected from $C_2$–$C_8$ alkyl;
$R_6$ is selected from the group consisting of H and the L-isomer (amino acid convention) of $R_7$—$(CH_2)_n$—$HC(NH_2)$—CO—;
wherein
n is an integer from 0 to 3;
$R_7$ is selected from the group consisting of $C_3$–$C_6$ alkyl and unsubstituted aryl, wherein said unsubstituted aryl is independently selected in each instance from the group consisting of phenyl, biphenyl, and naphthyl;
X is independently selected in each instance from the group consisting of trans, trans >C=CH—HC=C<, trans >C=C<, and >C*H—$(CH_2)_m$—HC*< where "*" indicates a chiral carbon atom and $R_3$ and $R_4$ are oriented L- and D-(amino acid convention) at these respective chiral centers; and
m=0, 1 or 2, or
a pharmaceutically acceptable salt, solvate or prodrug thereof.

59. The method of claim 58 wherein
$R_1$, $R_2$ and $R_5$ are H;
$R_3$ and $R_4$ are independently selected from the group consisting of n-butyl, n-amyl or n-hexyl;
$R_6$ is selected from the group consisting of L-phenylglycine and L-valine; and
X is selected from the group consisting of trans,trans >C=CH—HC=C<, trans >C=C<, >C*H—$(CH_2)_2$—C*H<, or >C*H—H*C< (wherein the "*" indicates a chiral carbon).

60. A method of treating a mammal with salt-sensitive, essential hypertension, comprising administering to the mammal a pharmaceutically effective amount of a compound of the formula:

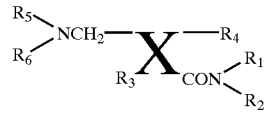

wherein:
$R_1$, $R_2$ and $R_5$ are independently selected from the group consisting of H and $C_1$–$C_2$ alkyl;
$R_3$ and $R_4$ are selected $C_2$–$C_8$ alkyl;
$R_6$ is selected from the group consisting of H and the L-isomer (amino acid convention) of $R_7$—$(CH_2)_n$—$HC(NH_2)$—CO—;
wherein
n is an integer from 0 to 3;
$R_7$ is selected from the group consisting of $C_3$–$C_6$ alkyl and unsubstituted aryl, wherein said unsubstituted aryl is independently selected in each instance from the group consisting of phenyl, biphenyl, and naphthyl;
X is independently selected in each instance from the group consisting of trans, trans >C=CH—HC=C<, trans >C=C<, and >C*H—$(CH_2)_m$—HC*< where "*" indicates a chiral carbon atom and $R_3$ and $R_4$ are oriented L- and D-(amino acid convention) at these respective chiral centers; and
m=0, 1 or 2, or
a pharmaceutically acceptable salt, solvate or prodrug thereof.

61. The method of claim 60 wherein
$R_1$, $R_2$ and $R_5$ are H;
$R_3$ and $R_4$ are independently selected from the group consisting of n-butyl, n-amyl or n-hexyl;
$R_6$ is selected from the group consisting of L-phenylglycine or L-valine; and
X is selected from the group consisting of trans,trans >C=CH—HC=C<, trans >C=C<, >C*H—$(CH_2)_2$—C*H<, and >C*H—H*C< (wherein the "*" represents a chiral carbon).

62. A method of treating a mammal with insulin resistance of Type 2 diabetes mellitus, comprising administering to the mammal a pharmaceutically effective amount of a compound of the formula:

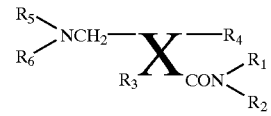

wherein:
$R_1$, $R_2$ and $R_5$ are independently selected from the group consisting of H and $C_1$–$C_2$ alkyl;
$R_3$ and $R_4$ are selected from $C_2$–$C_8$ alkyl;
$R_6$ is selected from the group consisting of H and the L-isomer (amino acid convention) of $R_7$—$(CH_2)_n$—$HC(NH_2)$—CO—;
wherein
n is an integer from 0 to 3;
$R_7$ is selected from the group consisting of $C_3$–$C_6$ alkyl and unsubstituted aryl, wherein said unsubstituted aryl is independently selected in each instance from the group consisting of phenyl, biphenyl, and naphthyl;
X is independently selected in each instance from the group consisting of trans, trans >C=CH—HC=C<, trans >C=C<, and >C*H—$(CH_2)_m$—HC*< where "*" indicates a chiral carbon atom and $R_3$ and $R_4$ are oriented L- and D-(amino acid convention) at these respective chiral centers; and
m=0, 1 or 2, or
a pharmaceutically acceptable salt, solvate or prodrug thereof.

63. The method of claim 62 wherein
$R_1$, $R_2$ and $R_5$ are H;
$R_3$ and $R_4$ are independently selected from the group consisting of n-butyl, n-amyl or n-hexyl;
$R_6$ is selected from the group consisting of L-phenylglycine and L-valine; and
X is selected from the group consisting of trans,trans >C=CH—HC=C<, trans >C=C<, >C*H—$(CH_2)_2$—C*H<, and >C*H—H*C< (wherein the "*" represents a chiral carbon).

64. A method of treating a mammal affected with pre-eclampsia/eclampsia, comprising administering to the mammal a pharmaceutically effective amount of a compound of the formula:

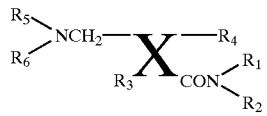

wherein:
R$_1$, R$_2$ and R$_5$ are independently selected from the group consisting of H and C$_1$–C$_2$ alkyl;
R$_3$ and R$_4$ are selected from C$_2$–C$_8$ alkyl;
R$_6$ is selected from the group consisting of H and the L-isomer (amino acid convention) of R$_7$—(CH$_2$)$_n$—HC(NH$_2$)—CO—;
wherein
n is an integer from 0 to 3;
R$_7$ is selected from the group consisting of C$_3$–C$_6$ alkyl and unsubstituted aryl, wherein said unsubstituted aryl is independently selected in each instance from the group consisting of phenyl, biphenyl, and naphthyl;
X is independently selected in each instance from the group consisting of trans, trans >C=CH—HC=C<, trans >C==C<, and >C*H—(CH$_2$)$_m$—HC*< where "*" indicates a chiral carbon atom and R$_3$ and R$_4$ are oriented L- and D-(amino acid convention) at these respective chiral centers; and
m=0, 1 or 2, or
a pharmaceutically acceptable salt, solvate or prodrug thereof.

65. The method of claim 64 wherein
R$_1$, R$_2$ and R$_5$ are H;
R$_3$ and R$_4$ are independently selected from the group consisting of n-butyl, n-amyl or n-hexyl;
R$_6$ is selected from the group consisting of L-phenylglycine and L-valine; and
X is selected from the group consisting of trans,trans >C=CH—HC=C<, trans >C=C<, >C*H—(CH$_2$)$_2$—C*H<, and >C*H—H*C< (wherein the "*" represents a chiral carbon).

66. The compound of claim 1, wherein
R$_1$, R$_2$ and R$_5$ are hydrogen;
R$_3$ and R$_4$ are n-butyl;
R$_6$ is L-phenylglycine; and
X is trans, trans >C=CH—HC=C<.

67. The pharmaceutical composition of claim 56, wherein
R$_1$, R$_2$ and R$_5$ are hydrogen;
R$_3$ and R$_4$ are n-butyl;
R$_6$ is L-phenylglycine; and
X is trans, trans >C=CH—HC=C<.

68. The method of claim 58, wherein
R$_1$, R$_2$ and R$_5$ are hydrogen;
R$_3$ and R$_4$ are n-butyl;
R$_6$ is L-phenylglycine; and
X is trans, trans >C=CH—HC=C<.

69. The method of claim 60, wherein
R$_1$, R$_2$ and R$_5$ are hydrogen;
R$_3$ and R$_4$ are n-butyl;
R$_6$ is L-phenylglycine; and
X is trans, trans >C=CH—HC=C<.

70. The method of claim 62, wherein
R$_1$, R$_2$ and R$_5$ are hydrogen;
R$_3$ and R$_4$ are n-butyl;
R$_6$ is L-phenylglycine; and
X is trans, trans >C=CH—HC=C<.

71. The method of claim 64, wherein
R$_1$, R$_2$ and R$_5$ are hydrogen;
R$_3$ and R$_4$ are n-butyl;
R$_6$ is L-phenylglycine; and
X is trans, trans >C=CH—HC=C<.

* * * * *

UNITED STATES PATENT AND TRADEMARK OFFICE
CERTIFICATE OF CORRECTION

PATENT NO. : 6,455,734 B1
DATED : September 24, 2002
INVENTOR(S) : Ibert Clifton Wells It is certified that error appears in the above-identified patent and that said Letters Patent is hereby corrected as shown below:

Column 3,
Line 42, delete "text" and insert -- tert --.

Column 7,
Line 59, delete "=" between "C*H" and "$CH_2$" and insert -- - --.

Column 10,
Line 3, delete "cis" and insert -- cis,cis- --.
Line 4, delete "grid" and insert -- acid --.

Column 11,
Line 6, delete "-4 -" and insert -- -4- --.
Line 16, delete "300" and insert -- 30° --.
Line 34, delete "butyl-4-trans," and insert -- butyl-2,4-trans, --.

Column 12,
Line 20, delete "$(C)_n$" and insert -- $(CH_2)_n$ --.

Column 17,
Line 18, delete "di-amylpentanoic" and insert -- di-n-amylpentanoic --.

Column 20,
Line 26, should not begin a new paragraph. Paragraph that begins "In some instances…" should continue paragraph on Line 25.

Column 22,
Line 55, delete "<CH" and insert -- >C --.

Signed and Sealed this

Twenty-fourth Day of June, 2003

JAMES E. ROGAN
*Director of the United States Patent and Trademark Office*